US009178193B2

(12) United States Patent
Ahn et al.

(10) Patent No.: US 9,178,193 B2
(45) Date of Patent: Nov. 3, 2015

(54) SUB-BATTERY PACK, BATTERY PACK HAVING THE SUB-BATTERY PACK, PORTABLE ULTRASONIC SCANNING APPARATUS USING THE SUB-BATTERY PACK AND BATTERY PACK, AND CART CARRYING THE SUB-BATTERY PACK, BATTERY PACK AND PORTABLE ULTRASONIC SCANNING APPARATUS

(71) Applicant: SAMSUNG MEDISON CO., LTD., Gangwon-do (KR)

(72) Inventors: Mi Jeoung Ahn, Seoul (KR); Jae Moon Jo, Seongnam-si (KR); Sangwon Bang, Seoul (KR)

(73) Assignee: SAMSUNG MEDISON CO., LTD., Hongcheon-gun, Gangwon-do (KR)

( * ) Notice: Subject to any disclaimer, the term of this patent is extended or adjusted under 35 U.S.C. 154(b) by 237 days.

(21) Appl. No.: 13/913,203

(22) Filed: Jun. 7, 2013

(65) Prior Publication Data

US 2013/0330588 A1    Dec. 12, 2013

(30) Foreign Application Priority Data

Jun. 8, 2012    (KR) .................. 10-2012-0061710

(51) Int. Cl.
*H01M 2/10*    (2006.01)
*A61B 8/00*    (2006.01)
*H01M 10/48*    (2006.01)

(52) U.S. Cl.
CPC .......... *H01M 2/1016* (2013.01); *A61B 8/4427* (2013.01); *A61B 8/4444* (2013.01); *A61B 8/56* (2013.01); *H01M 2/1022* (2013.01); *H01M 2/1027* (2013.01); *H01M 10/488* (2013.01); *H01M 2220/30* (2013.01)

(58) Field of Classification Search
CPC .......... H01M 2/1016; H01M 2/1022; H01M 2/1027; H01M 2220/30
USPC .......................................... 429/99
See application file for complete search history.

(56) References Cited

U.S. PATENT DOCUMENTS 5,149,603 A * 9/1992 Fleming et al. .................. 429/98
5,295,485 A * 3/1994 Shinomura et al. ........... 600/443

(Continued)

FOREIGN PATENT DOCUMENTS

| JP | 08-065919 | 3/1996 |
| JP | 09-266636 | 10/1997 |

(Continued)

OTHER PUBLICATIONS

Korean Office Action issued in Korean Patent Application No. KR 10-2012-0061710 dated Jun. 21, 2013.

*Primary Examiner* — Stewart Fraser
(74) *Attorney, Agent, or Firm* — McDermott Will & Emery LLP

(57) ABSTRACT

A battery pack includes a case, at least one receptacle defined in the case and configured to accommodate at least one battery that supplies power to a portable ultrasonic scanning apparatus, at least one first terminal installed to the at least one receptacle, the first terminal coming into contact with a terminal of the battery when the battery is accommodated in the at least one receptacle, and a second terminal electrically connected to the at least one first terminal, the second terminal being electrically connected to the portable ultrasonic scanning apparatus.

15 Claims, 12 Drawing Sheets

(56) References Cited

U.S. PATENT DOCUMENTS

| | | | |
|---|---|---|---|
| 5,931,791 A * | 8/1999 | Saltzstein et al. | 600/513 |
| 6,695,777 B2 * | 2/2004 | Solomon et al. | 600/437 |
| 2003/0022060 A1 * | 1/2003 | Solomon et al. | 429/123 |
| 2010/0249600 A1 * | 9/2010 | Kudoh et al. | 600/459 |

FOREIGN PATENT DOCUMENTS

| | | |
|---|---|---|
| JP | 2005-511113 A | 4/2005 |
| KR | 10-2008-0075646 A | 8/2008 |
| KR | 2011-0064278 A | 6/2011 |

* cited by examiner

SUB-BATTERY PACK, BATTERY PACK HAVING THE SUB-BATTERY PACK, PORTABLE ULTRASONIC SCANNING APPARATUS USING THE SUB-BATTERY PACK AND BATTERY PACK, AND CART CARRYING THE SUB-BATTERY PACK, BATTERY PACK AND PORTABLE ULTRASONIC SCANNING APPARATUS

CROSS-REFERENCE TO RELATED APPLICATION

This application claims the benefit of priority to Korean Patent Applications No. 2012-0061710, filed on Jun. 8, 2012 in the Korean Intellectual Property Office, the disclosure of which is incorporated herein by reference.

TECHNICAL FIELD

Present disclosure relates to a sub-battery pack and a battery pack to supply power to a portable ultrasonic scanning apparatus, the portable ultrasonic scanning apparatus to receive power from the sub-battery pack or the battery pack, and a cart to conveniently move the battery pack and the portable ultrasonic scanning apparatus.

BACKGROUND

Ultrasonic scanning apparatuses generate ultrasonic waves and receive the ultrasonic waves reflected from a human body, thereby judging the presence or absence of any diseases or other abnormalities of the human body.

Ultrasonic scanning apparatuses are mainly installed and used in, e.g., doctor's offices and exam rooms of hospitals. Despite needs for moving the ultrasonic scanning apparatuses, and it is not easy to transport the ultrasonic scanning apparatuses from hospitals because of significant volume and weight thereof. Thus, patients, who are not able to move about freely and thus have difficulty in visiting hospitals may have difficulty in getting a ultrasonic scan.

To overcome the above-described restriction in transportation, a need exists for providing portable ultrasonic scanning apparatuses having convenience in carrying.

SUMMARY

An aspect of the present disclosure provides a sub-battery pack and a battery pack, which may supply power to a portable ultrasonic scanning apparatus from positions outside thereof, the portable ultrasonic scanning apparatus using the sub-battery pack or the battery pack, and a cart to move the battery pack and the portable ultrasonic scanning apparatus.

One aspect of the disclosure relates to a battery pack including a case, at least one receptacle defined in the case and configured to accommodate at least one battery that supplies power to a portable ultrasonic scanning apparatus, at least one first terminal installed to the at least one receptacle, the first terminal coming into contact with a terminal of the battery when the battery is accommodated in the at least one receptacle, and a second terminal electrically connected to the at least one first terminal, the second terminal being electrically connected to the portable ultrasonic scanning apparatus.

The at least one receptacle may include plural receptacles partitioned from one another.

The respective receptacles may have different sizes of receiving spaces to accommodate different sizes of batteries.

The respective receptacles may have different widths or lengths.

The first terminal may be installed to a wall surface of the at least one receptacle.

The second terminal may be installed to an outer surface of the case.

The at least one first terminal may include plural first terminals, and the plural first terminals may be independent of one another with respect to the second terminal.

The at least one first terminal may include plural first terminals, the plural first terminals are connected to one another in parallel, and the second terminal may be connected in series to the plural first terminals.

Another aspect of the present disclosure encompasses a battery pack including a first sub-battery pack including a first case, a first receptacle defined in the first case to accommodate a battery that supplies power to a portable ultrasonic scanning apparatus, and a first coupler installed to the exterior of the first case, and a second sub-battery pack including a second case, a second receptacle defined in the second case to accommodate a battery that supplies power to the portable ultrasonic scanning apparatus, and a second coupler installed to the exterior of the second case to enable coupling between the first sub-battery pack and the second sub-battery pack.

Each of the first and second sub-battery packs may include a first terminal installed to the first or second receptacle to come into contact with a terminal of the battery when the battery is mounted in the first or second receptacle, and a second terminal electrically connected to the first terminal, the second terminal being electrically connected to the portable ultrasonic scanning apparatus.

The first coupler may include a boss, and the second coupler may include a groove for sliding coupling of the boss.

The first and second couplers may be formed near corners of vertical outer surface edges of the first and second cases.

Another aspect of the present disclosure provides a sub-battery pack including a case, a receptacle defined in the case and configured to accommodate a battery that supplies power to a portable ultrasonic scanning apparatus, a first terminal installed to the receptacle, the first terminal coming into contact with a terminal of the battery when the battery is accommodated in the receptacle, a second terminal electrically connected to the first terminal, the second terminal being electrically connected to the portable ultrasonic scanning apparatus, and a coupler installed to the exterior of the case to allow the sub-battery pack to be coupled to another sub-battery pack.

The coupler may include a boss for sliding coupling with a groove formed in another sub-battery pack, or a recess for sliding coupling with a boss formed at another sub-battery pack.

The coupler may be formed near a corner of a vertical outer surface edge of the case.

Another aspect of the present disclosure relates to a portable ultrasonic scanning apparatus including a probe to generate ultrasonic waves and receive the ultrasonic waves reflected from a subject, an image processor to generate image data by processing ultrasonic data transmitted from the probe, a display unit to display the image data, and an externally located power source unit connected to a battery pack, in which a plurality of batteries is accommodated, to supply power to the probe, the image processor, and the display unit.

The portable ultrasonic scanning apparatus may further include a controller to judge a remaining charge of all of the plurality of batteries accommodated in the battery pack.

The portable ultrasonic scanning apparatus may further include a plurality of relays to turn on or off electric connection between each battery accommodated in the battery pack and the power source unit, and a controller to judge a remaining charge of each battery, and if the remaining charge of a single battery electrically connected to the power source unit is a reference value or less, the controller may drive the plurality of relays to electrically connect another battery and the power source unit to each other and disconnect electric connection between the single battery and the power source unit.

The display unit may display the remaining charge of the single battery, may warn a user that the remaining charge is the reference value or less, and may inform the user of replacement of the battery that supplies power to the power source unit.

The portable ultrasonic scanning apparatus may further include a plurality of relays to turn on or off electric connection between each battery accommodated in the battery pack and the power source unit, and a controller to judge a remaining charge of each battery, and if the remaining charge of a single battery electrically connected to the power source unit is a reference value or less, the controller may drive the plurality of relays to electrically connect another battery and the power source unit to each other and may perform charging of the single battery.

The portable ultrasonic scanning apparatus may further include a plurality of relays to turn on or off electric connection between each battery accommodated in the battery pack and the power source unit, and a controller to electrically connect a battery, selected based on at least one workflow or application, and the power source to each other by driving the plurality of relays upon execution of the at least one workflow or application.

The portable ultrasonic scanning apparatus may further include a memory to store a list of batteries to be used upon execution of each application or workflow.

Another aspect of the present disclosure relates to a cart for a portable ultrasonic scanning apparatus. The cart includes a support stand on which the portable ultrasonic scanning apparatus is placed, the support stand having a mounting recess in which a battery pack accommodating at least one battery is detachably mounted, and a plurality of casters attached to the bottom of the support stand.

A third terminal may be installed to the mounting recess and may come into contact with a terminal of the battery pack when the battery pack is mounted in the mounting recess, and the third terminal may be electrically connected to a fourth terminal installed to the support stand, the fourth terminal being connected to a power source unit of the portable ultrasonic scanning apparatus.

A plurality of relays may be installed between the third terminal and the fourth terminal to turn on or off electric connection between each battery accommodated in the battery pack and a power source unit of the portable ultrasonic scanning apparatus, the plurality of relays being driven by the portable ultrasonic scanning apparatus.

Still another aspect of the present disclosure relates to a cart including a support stand having a plurality of casters attached to the bottom thereof, and at least one receptacle defined in an upper surface thereof to accommodate a battery that supplies power to a portable ultrasonic scanning apparatus, and a board hinged to the top of the support stand, on which the portable ultrasonic scanning apparatus is placed.

An LED display unit may be installed to a front surface of the board to display a charged state of the battery accommodated in the receptacle.

BRIEF DESCRIPTION OF THE DRAWINGS

These and/or other aspects of the present disclosure will become apparent and more readily appreciated from the following description of the embodiments, taken in conjunction with the accompanying drawings of which.

DETAILED DESCRIPTION

Figure 1:
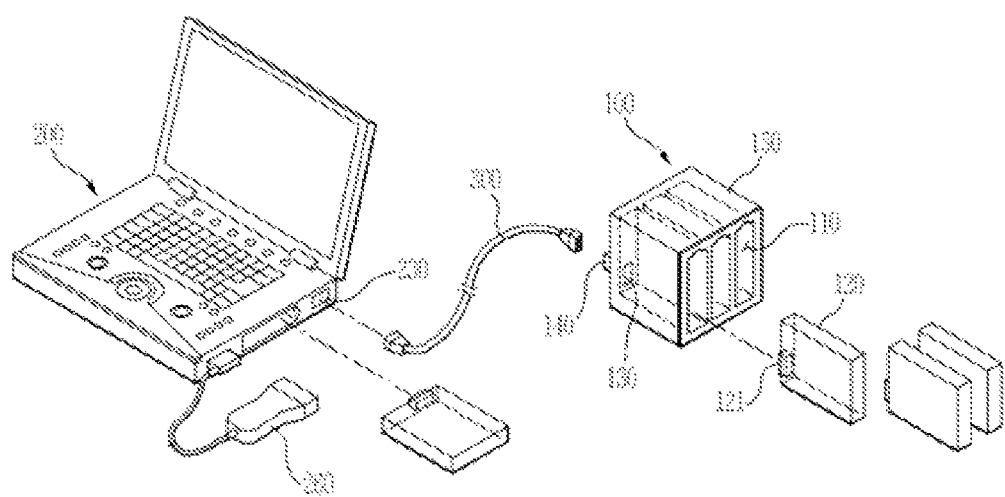
FIG. 1 is a view illustrating a battery pack and a portable ultrasonic scanning apparatus according to an embodiment of the present disclosure.

Reference will now be made in detail to the embodiments of the present disclosure, examples of which are illustrated in the accompanying drawings, wherein like reference numerals refer to like elements throughout.

Figure 2:
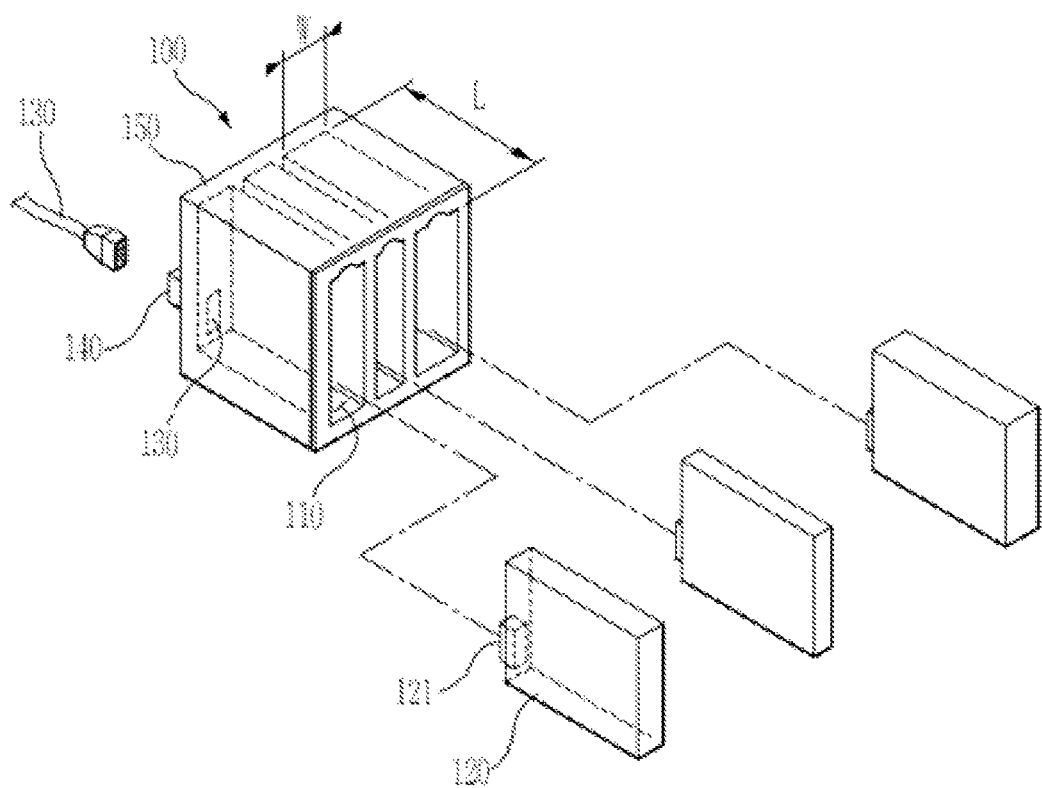
FIG. 2 is a perspective view illustrating a battery pack having different widths of receptacles.
Figure 3:
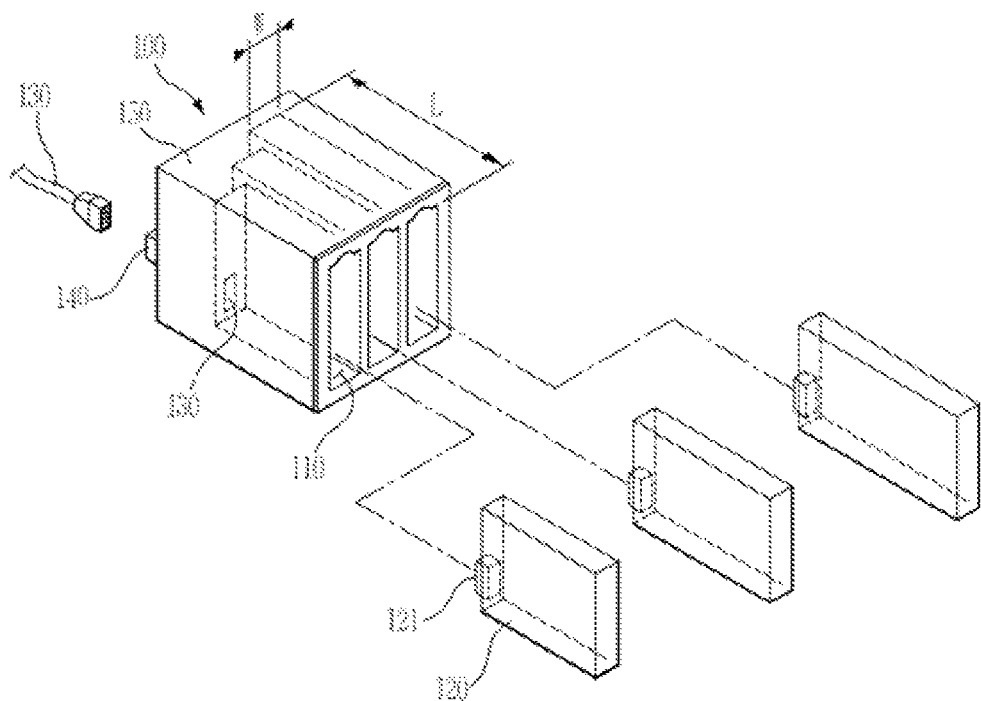
FIG. 3 is a perspective view illustrating a battery pack having different lengths of receptacles.

FIGS. 1 to 3 illustrate a battery pack and a portable ultrasonic scanning apparatus according to an embodiment of the present disclosure. As illustrated in FIG. 1, the battery pack 100 according to the embodiment of the present disclosure is connected to a power port 230 of the portable ultrasonic scanning apparatus 200 via a cable 300 to supply power to the portable ultrasonic scanning apparatus 200. The battery pack 100 includes a case 150, and a plurality of receptacles 110 defined in the case 150.

The receptacles 110 are partitioned from one another, and a battery 120 to supply power to the portable ultrasonic scanning apparatus 200 is accommodated in each receptacle 110. The battery 120 may be fabricated to have the same size and function as those of an internal battery (240 in FIG. 4) of the portable ultrasonic scanning apparatus 200. In this case, the battery 120 may be accommodated in the battery pack 100, or may be directly detachably attached to the portable ultrasonic scanning apparatus 200. Also, the respective receptacles 110 may have the same size to accommodate the same size of batteries (i.e. batteries having the same storage capacity), or may have different sizes to accommodate different sizes of batteries (i.e. batteries having different storage capacities).

As illustrated in FIG. 2, the respective receptacles 110 may have the same length L, but have different widths W, to accommodate batteries having the same length L and various widths W. Alternatively, as illustrated in FIG. 3, the respective receptacles 110 may have the same width W, but have different lengths L, to accommodate batteries having the same width W and various lengths L. Also, the respective receptacles 110 may have different widths W and lengths L, to accommodate batteries having different widths W and lengths L.

Although the present embodiment exemplifies partitions as being formed between the respective receptacles, the receptacles may be partitioned by guide slots configured to assist accommodation of batteries without partitions therebetween.

A first terminal 130 is installed on an inner rear surface of each receptacle 110. The first terminal 130 is adapted to come into contact with a terminal 121 of the battery 120 when the battery 120 is mounted in the receptacle 110. Although the present embodiment exemplifies the first terminal 130 as being installed on the inner rear surface of the receptacle 110, the position of the first terminal 130 is not limited thereto, and may be installed anywhere on an inner wall surface of the receptacle 110.

The first terminal 130 is electrically connected to a second terminal 140 that is installed on an outer rear surface of the case 150. Although the present embodiment exemplifies the second terminal 140 as being installed on the outer rear surface of the case 150, the position of the second terminal 140 is not limited thereto, and may be installed anywhere on an outer wall surface of the case 150.

The second terminal 140 may be connected to the power port 230 of the portable ultrasonic scanning apparatus 200 via the cable 300, or may come into contact with a third terminal 440 of a cart 400 when the battery pack 100 is mounted to the cart 400 that will be described hereinafter. Also, the second terminal 140 may be connected to a charge cable (not shown) that is used to charge the batteries.

Since the plural first terminals 130 connected to the second terminal 140 are separate from each other, the portable ultrasonic scanning apparatus 200 is connected to only one battery of a plurality of batteries 120 accommodated in the battery pack 100, even if the battery pack 100 is electrically connected to the portable ultrasonic scanning apparatus 200.

That is, plural pins (or holes) provided at the second terminal 140 are independently connected to the respective first terminals 130, and the cable 300 connecting the portable ultrasonic scanning apparatus 200 and the second terminal 140 to each other has lines corresponding to the plurality of pins (or holes) of the second terminal 140. As such, an independent connection relationship between the first terminals is maintained even if the second terminal 140 and the portable ultrasonic scanning apparatus 200 are connected to each other via the cable 300.

Figure 4:
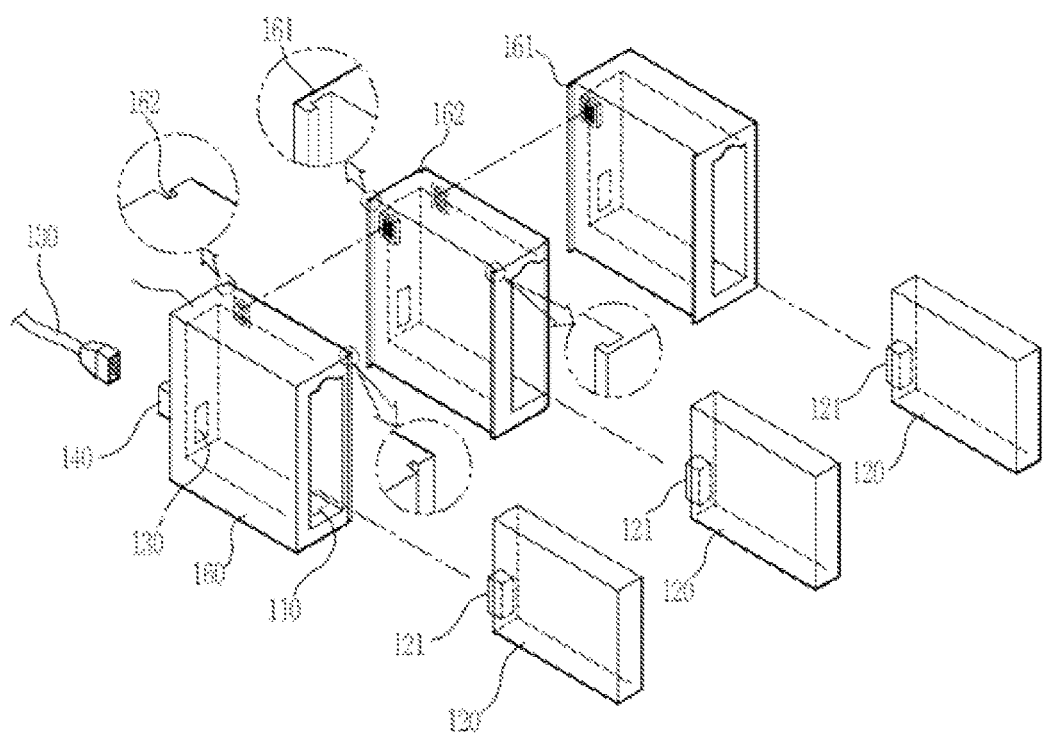
FIG. 4 is a perspective view illustrating an assembly type battery pack.

Additionally, the portable ultrasonic scanning apparatus 200 includes a plurality of relays (220 in FIG. 4) to electrically connect or disconnect the respective batteries 120 to or from a power source unit (210 in FIG. 4). The portable ultrasonic scanning apparatus 200 may selectively drive the relays 220 so as to be connected to only one battery 120 with disconnection from the other batteries 120. This will hereinafter be described in detail.

Although the present embodiment exemplifies that the single second terminal 140 is connected to the plurality of first terminals 130, the same number of second terminals 140 as that of the first terminals 130 may be provided such that the first and second terminals 130 and 140 are connected to each other in a one to one ratio.

Also, although the present embodiment exemplifies that the plural first terminals 130 connected to the second terminal 140 are separate from each other, the second terminal 140 may be connected in series to all the first terminals 130 that are connected to one another in parallel, such that all batteries accommodated in the battery pack 100 are available as a single battery.

The battery pack according to the embodiment of the present disclosure may be of an assembly type (or a detachable type) as illustrated in FIG. 4. That is, the battery pack may be divided into a plurality of sub-battery packs 160, and one sub-battery pack 160 may have one receptacle 110. Also, each sub-battery pack is provided with a first terminal and a second terminal, and one or more couplers 161 and 162.

The couplers include a boss 161 and a groove 162. Two sub-battery packs are coupled to each other as the boss 161 formed at one sub-battery pack slides into the groove 162 formed at the other sub-battery pack.

To constitute a single battery pack using the plurality of sub-battery packs 160, two sub-battery packs located at both ends of the battery pack 100 have one coupler at only one outer surface thereof, and each sub-battery pack located between the two sub-battery packs has two couplers at both outer surfaces thereof.

As illustrated in FIG. 4, assuming that a single battery pack has three sub-battery packs, one sub-battery pack located at a left end of the battery pack 100 is provided with the groove 162 near a corner of a right vertical edge thereof, and another sub-battery pack located at a right end of the battery pack 100 is provided with the boss 161 near a corner of a left vertical edge thereof.

Also, a center sub-battery pack of the battery pack is provided near a corner of a left vertical edge thereof with the boss 161 and near a corner of a right vertical edge thereof with the groove 162, so as to be coupled to the groove 162 formed at the sub-battery pack provided at the left end of the battery pack 100 and the boss 161 formed at the sub-battery pack provided at the right end of the battery pack 100.

Although FIG. 4 illustrates a sliding coupling between the boss 161 and the groove 162 to form the assembly type battery pack, the respective sub-battery packs may be coupled to one another in different ways.

Also, unlike FIG. 4, all sub-battery packs may be respectively provided at both surfaces thereof with the boss 161 and the groove 162, which ensures assembly of the sub-battery packs without distinction thereof.

As such, the battery pack 100 according to the embodiment of the present disclosure is adapted to supply power to the portable ultrasonic scanning apparatus 200 using at least one battery, which may lengthen a use time of the portable ultrasonic scanning apparatus 200 without frequent charge of the internal battery of the portable ultrasonic scanning apparatus 200.

Figure 5:
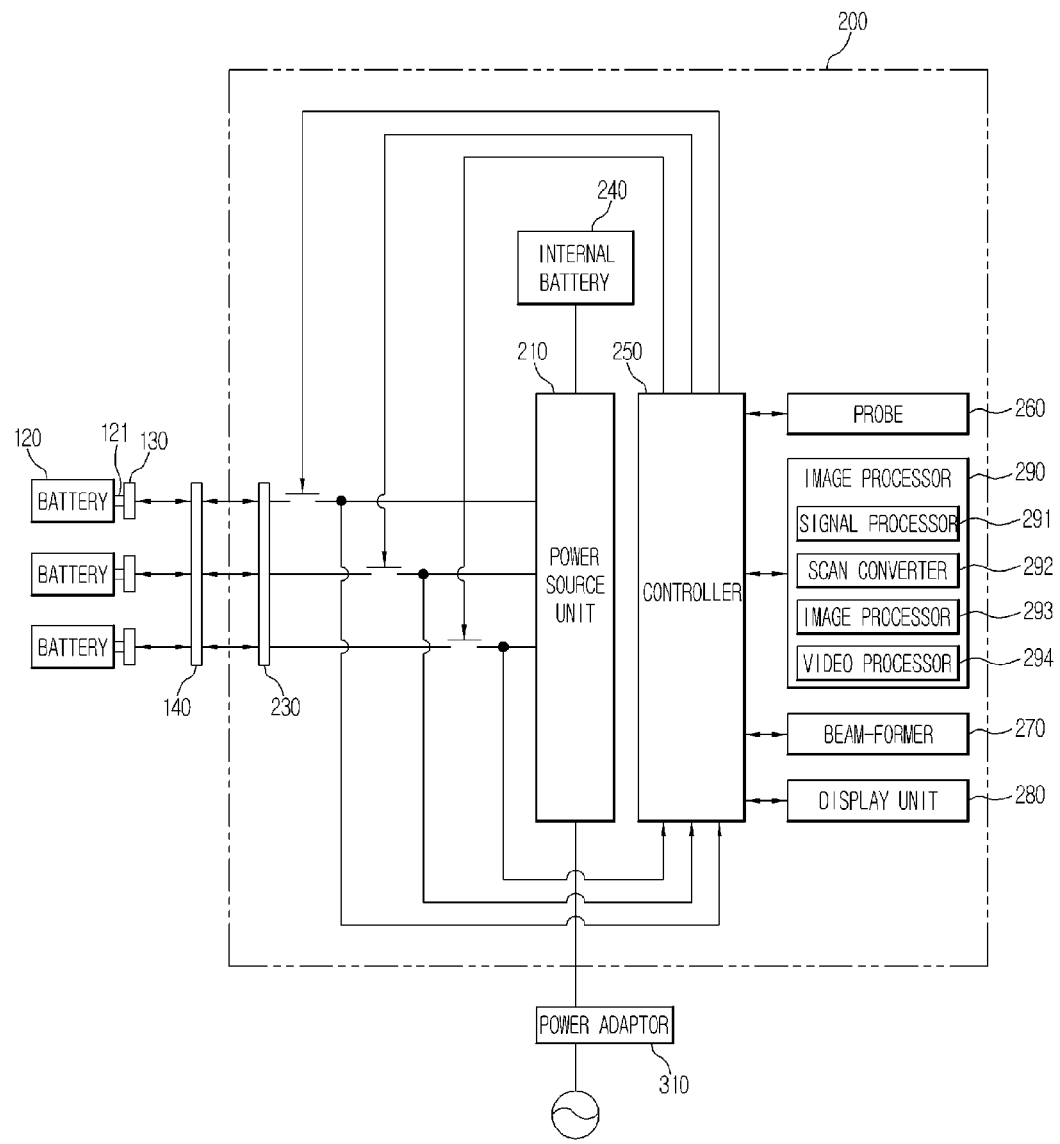
FIG. 5 is a view illustrating a connection relationship between a control block of a portable ultrasonic scanning apparatus and a battery pack according to an embodiment of the present disclosure.
Figure 6:
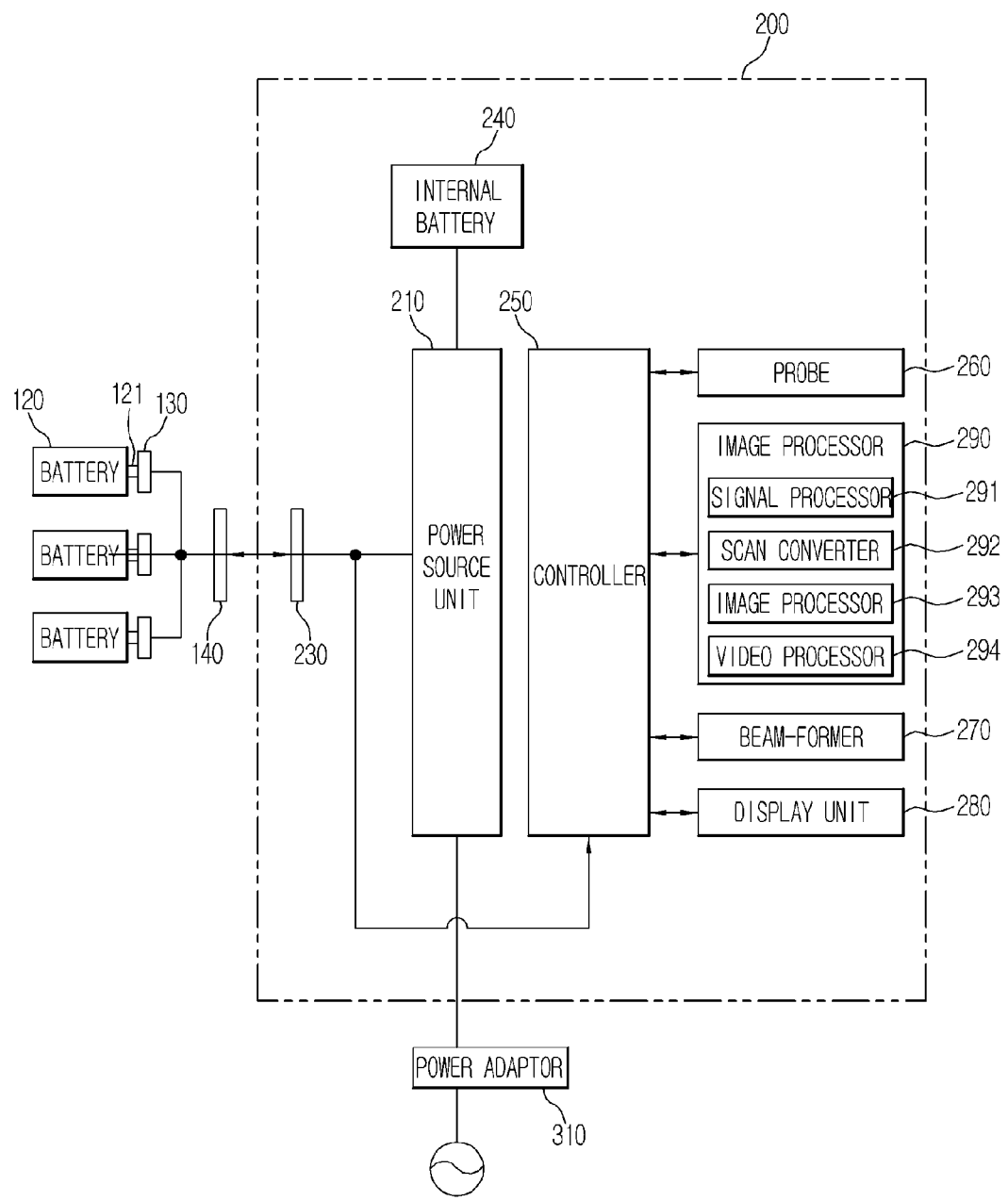
FIG. 6 is a view illustrating a battery pack having electrically connected receptacles and a portable ultrasonic scanning apparatus connected thereto in a configuration different from that of FIG. 5.

FIGS. 5 and 6 illustrate the battery pack and the portable ultrasonic scanning apparatus according to the embodiment of the present disclosure. As illustrated in FIG. 5, the portable ultrasonic scanning apparatus 200 according to the embodiment of the present disclosure includes a probe 260, beam-former 270, image processor 290, display unit 280, relays 220, power port 230, power source unit 210, memory 241, and controller 250.

The probe 260 includes 1D, 2D or 3D inverters. The probe 260 transmits ultrasonic beams (or ultrasonic signals), generated as each inverter appropriately delays pulse signals, to a subject through a transmission scan line. The ultrasonic signals (i.e. ultrasonic echo signals) reflected from the subject are inputted to the respective inverters with different reception intervals to thereby be inverted into electric signals.

The beam-former 270 receives the signals from the probe 260 and changes the received analog signals into digital signals. Also, the beam-former 270 generates focused signals from the received digital signals.

The image processor 290 includes a signal processor 291, scan converter 292, image processor 293, and video processor 294. The signal processor 291 forms ultrasonic image data by performing envelope detection processing that detects the strength of the focused signals from the beam-former 270.

The scan converter 292 performs a scan conversion of the ultrasonic image data outputted from the signal processor 291.

The image processor 293 performs various image processings (for example, B-mode image processing and Doppler image processing) on the scan-converted ultrasonic image data.

The video processor 294 performs a RGB processing of the ultrasonic image data transmitted from the image processor 293.

The display unit 280 displays an ultrasonic image using the ultrasonic image data outputted from the video processor 294.

The relays 220 are connected between the power port 230 and the power source unit 210 to connect or disconnect the respective batteries 120 accommodated in the battery pack 100 to or from the power source unit 210. The relays 220 are turned on or off in response to a control instruction of the controller 250. The relays 220 are not used in the portable ultrasonic scanning apparatus 200 in which the power source unit 210 receives power from the second terminal 140 that is connected in series to the parallel first terminals 130.

Although the present embodiment exemplifies use of the relays 220 to connect or disconnect the respective batteries 120 to or from the power source unit 210, other devices (for example, MOSFET switches) performing the same switching function as the relays 220 may be used instead of the relays 220.

The power port 230 is connected to the second terminal 140 of the battery pack 100 and a fourth terminal 450 of the cart 400 through the cable 300, and transmits power of the battery pack 100 to the power source unit 210.

The power source unit 210 may be connected to a commercial power source 320 through a power adaptor 310, or may be connected to the internal battery 240 so as to supply power to the above-described probe 260. The power source unit 210 may be connected to the battery pack 100 through the power port 230 to supply power to the above-described probe 260. Here, technology for supply of power to the above-described probe 260 via connection with the commercial power source 320 or the internal battery 240 is known, and thus a detailed description thereof will be omitted.

The power source unit 210 is connected to the second terminal 140 through the relays 220, the power port 230 and the cable 300. Here, the batteries 120 mounted in the battery pack 100 are separate from each other even if all of the relays 220, power port 230, cable 300 and second terminal 140 are connected to one another. As such, it may be possible to achieve connection between the power source unit 210 and only the single battery 120 by controlling On or Off operation of the relays 220. The On or Off operation of the relays 220 will hereinafter be described.

Although the present embodiment exemplifies the power source unit 210 as being connected to the single battery 120, the power source unit 210 may be connected to all the batteries 120 simultaneously. That is, when the second terminal 140 of the battery pack 100 is connected in series to all the first terminals 130 that are connected in parallel, and the power source unit 210 is connected to the second terminal 140, consequently, the power source unit 210 may be connected to all the batteries 120 simultaneously. In this case, it may be unnecessary to locate the relays 220 between the power source unit 210 and the power port 230, and the portable ultrasonic scanning apparatus 200 may utilize all the batteries 120 accommodated in the battery pack 100 as a single battery.

The power source unit 210 supplies charging power to a battery that requires charging if the internal battery 240 or the battery 120 accommodated in the battery pack 100 needs to be charged (for example, a remaining charge is 5% or less) and is connected to the commercial power source 320 through the power adaptor 310. Here, a method of judging the remaining charge of the internal battery 240 and a charging method are appreciated by one skilled in the art, and thus a detailed description thereof will be omitted. For example, Korean Patent Laid Open Publication No. 2000-0025198 discloses the method of judging the remaining charge. The controller 250 controls driving of the relays 220 during charging of the battery pack 100 as will be described hereinafter.

The power source unit 210 may have a circuit configuration to select one of the battery pack 100, internal battery 240, and commercial power source determined based on the order of priority as a power supply source if two or more of the battery pack 100, internal battery 240, and commercial power source are connected to one another, or may select one of the battery pack 100, internal battery 240, and commercial power source 320 as a power supply source in response to a control instruction of the controller 250. For example, if the battery pack 100 and the internal battery 240 are simultaneously connected to the power source unit 210, the power source unit 210 may be configured to preferentially use power of the battery pack 100.

The memory 241 stores a list of batteries connected to the power source unit 210 upon execution of each application or workflow embedded in the controller 250. This will hereinafter be described in detail.

The controller 250 controls general operations of the portable ultrasonic scanning apparatus 200. The controller 250 monitors the remaining charge of the battery pack 100 and the internal battery 240, and performs charging of the battery pack 100 and the internal battery 240 as necessary. Here, operation related to the internal battery 240 will be appreciated by one skilled in the art, and thus a detailed description thereof will be omitted.

The controller 250 checks voltages of the first terminals 130 of the battery pack 100 by sensing voltages of the relays 220, and judges whether or not the batteries 120 are mounted in the respective receptacles 110 of the battery pack 100. If the plurality of batteries 120 are accommodated in the battery pack 100, the controller 250 turns on the relay 220 connected between one of the batteries 120 and the power source unit 210, and turns off the other relays 220. Thereby, the power source unit 210 may be connected to one of the plurality of batteries 120 accommodated in the battery pack 100.

The controller 250 judges the remaining charge of the single battery 120 upon receiving power from the battery 120, and controls display of the remaining charge of the battery 120 on the display unit 280. Judgment of the remaining charge of the battery 120 and a display method will be appreciated by one skilled in the art, and thus a detailed description thereof will be omitted.

The controller 250 displays an alarm on the display unit 280 if the remaining charge of the battery 120 is less than or equal to a reference value (for example, if a remaining charge is 5% or less). If the remaining charge of the battery 120 to which power has been supplied is less than or equal to the reference value, the controller 250 turns on the relay 220 that connects another battery 120 and the power source unit 210 to each other, and turns off the relay 220 that connects the existing battery 120 and the power source unit 210 to each other.

As described above, if one battery is almost discharged, the controller 250 connects another battery to the power source unit 210, and disconnects the almost discharged battery from the power source unit 210. In this case, the connection sequence between the respective batteries 120 (i.e. the first terminals) and the power source unit 210 is predefined, and the controller 250 drives the relays 220 based on the sequence so as to sequentially connect each battery 120 to the power source unit 210.

The controller 250 may connect another battery to the power source unit 210 if the existing battery 120, which has been used to supply power to the power source unit 210, is almost discharged, and may perform charging of the existing battery 120 while maintaining connection between the existing battery 120 and the power source unit 210.

Once the battery 120 has been replaced, the controller 250 may display the replacement on the display unit 280.

Although the present embodiment exemplifies the power source unit 210 as being connected to the single battery 120, the power source unit 210 may be connected to all the batteries 120 as illustrated in FIG. 6. In this case, the controller 250 judges a remaining charge of all the batteries 120, and the display unit 280 displays the remaining charge of all the batteries 120.

Although the present embodiment exemplifies connection or disconnection between the battery and the portable ultrasonic scanning apparatus 200 based on charging or discharging of the battery, the portable ultrasonic scanning apparatus 200 may be connected to another battery based on an application or workflow executed in the portable ultrasonic scanning apparatus 200.

To this end, the memory 241 of the portable ultrasonic scanning apparatus 200 stores a list of batteries, according to which the batteries 120 are selected as a power source upon execution of each application or workflow, and the order of priority of each application or workflow is designated. As such, the battery is selected based on a top priority workflow or application among a plurality of applications or workflow.

For example, if three batteries are mounted in the battery pack and the lifespans of the respective batteries are respectively 10 min (battery A), 20 min (battery B) and 30 min (battery C), the battery C having the longest lifespan may be connected upon execution of workflow that requires a long time, such as high-resolution ultrasonography that closely checks the state of the fetus, and the battery A having the shortest lifespan may be connected upon execution of workflow that requires a short time, such as thyroid ultrasonography that examines the state of the thyroid. To this end, the memory 241 stores a list of workflow-battery, such as high-resolution ultrasonography-battery C and thyroid ultrasonography-battery A.

The portable ultrasonic scanning apparatus 200 according to the embodiment of the present disclosure is adapted to receive power from the battery pack 100 to which at least one battery 120 is mounted, and thus is operable for a long time even if the user does not frequently charge the internal battery 240.

Figure 7:
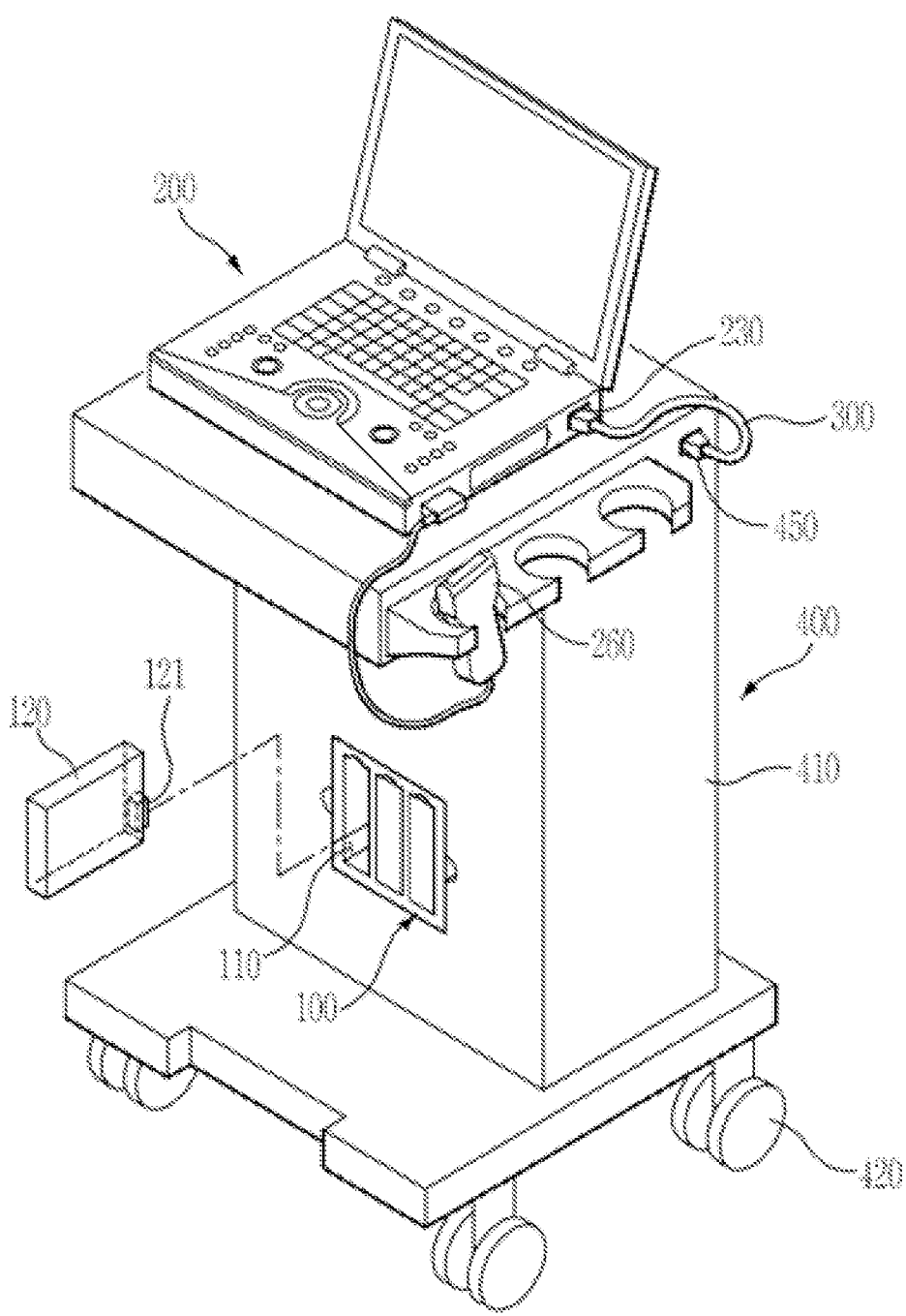
FIG. 7 is a perspective view illustrating a cart according to an embodiment of the present disclosure.
Figure 8:
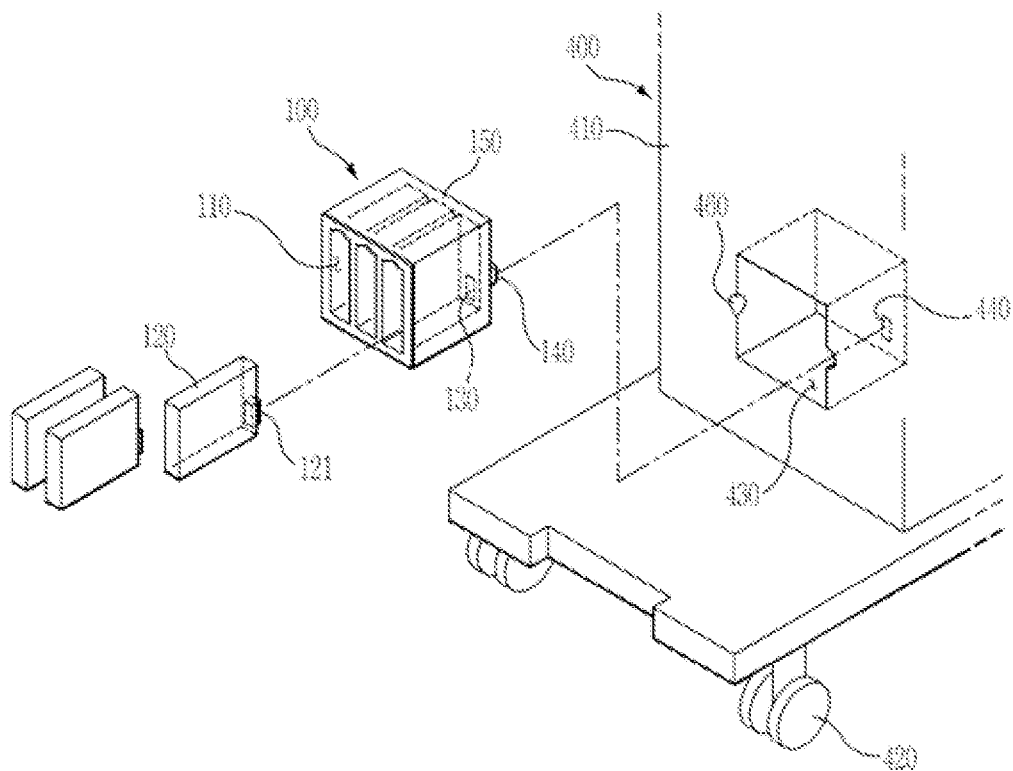
FIG. 8 is a view illustrating a mounting recess of the cart illustrated in FIG. 6.

FIGS. 7 and 8 illustrate a cart according to an embodiment of the present disclosure. As illustrated in FIGS. 7 and 8, the cart 400 according to the embodiment of the present disclosure includes a support stand 410 on which the portable ultrasonic scanning apparatus 200 is placed, and a plurality of casters 420 attached to the bottom of the support stand 410.

A mounting recess 430 is defined in a front surface of the support stand 410. The battery pack 100 containing the plurality of batteries 120 is accommodated in the mounting recess 430. Although the present embodiment exemplifies the mounting recess 430 as being defined in the front surface of the cart 400, the position of the mounting recess 430 is not limited thereto, and the mounting recess 430 may be formed in any other positions of the support stand 410. A recessed grip 460 is formed at the entrance of the mounting recess 430 to assist the user to easily grip the battery pack 100 upon attachment/detachment of the battery pack 100.

The third terminal 440 is installed on a rear surface of the mounting recess 430 so as to come into contact with the second terminal 140 of the battery pack 100 when the battery pack 100 is mounted in the mounting recess 430. Although the present embodiment exemplifies the third terminal 440 as being formed at the rear surface of the mounting recess 430, the position of the third terminal 440 is not limited thereto, and the third terminal 440 may be formed at any other positions of the mounting recess 430 so long as it corresponds to the second terminal 140 of the battery pack 100.

The third terminal 440 is connected to a fourth terminal 450 installed to the exterior of the support stand 410. The fourth terminal 450 is connected to the power port 230 of the portable ultrasonic scanning apparatus 200 via the cable 300. Although the present embodiment exemplifies the portable ultrasonic scanning apparatus 200 as including the relays 220, the relays 220 may be installed between the third terminal 440 and the fourth terminal 450, and may be driven in response to a control instruction of the controller 250 of the portable ultrasonic scanning apparatus 200.

Figure 9:
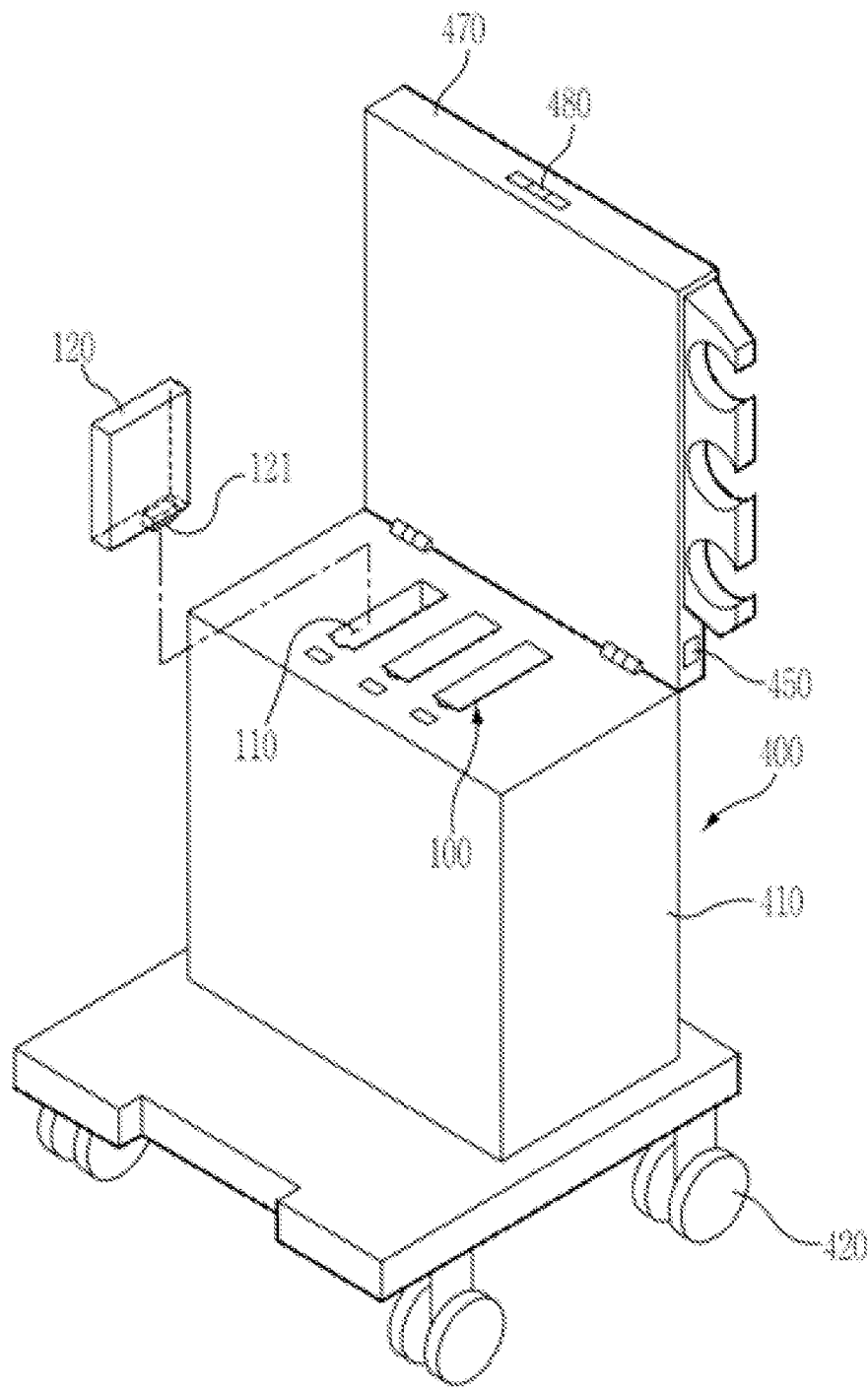
FIG. 9 is a view illustrating an alternative embodiment of the cart illustrated in FIG. 7.

Alternatively, the cart 400 may be configured as illustrated in FIG. 9. In the cart of FIG. 9, the cart 400 includes a board 470 on which the portable ultrasonic scanning apparatus 200 is placed, and the support stand 410 to support the board 470, and the board 470 and the support stand 410 are hinged to each other.

The receptacles 110 in which the batteries 120 are respectively accommodated are formed in an upper surface of the support stand 410. A first terminal (not shown) is installed to an inner lower surface of each receptacle 110. The first terminal is adapted to come into contact with the terminal 121 of the battery 120 when the battery 120 is mounted in the receptacle 110. Also, the first terminal is connected to the fourth terminal 450.

An Light Emitting Diode (LED) display unit 480 is installed on a front surface of the board 470 and serves to display a charging state of each battery 120 mounted in the receptacle 110. The LED display unit 480 is divided into three sections, and LEDs of the respective sections display whether the batteries 120 mounted in the three receptacles 110 are charged or discharged. For example, if the battery in the left receptacle is charged and the batteries in the center and right receptacles are discharged, the left LED of the LED display unit 480 may emit green light, and the center and right LEDs of the LED display unit 480 may emit red light.

The LED display unit 480 operates in response to the control instruction of the controller 250, and the judgment of a remaining charge of each battery, and other elements are identical to the above description related to the cart 400 of FIGS. 7 and 8.

Accordingly, the cart 400 according to the embodiment of the present disclosure may easily move the battery pack 100 having the at least one battery 120 and the portable ultrasonic scanning apparatus 200 adapted to receive power from the battery pack 100, and may ensure an extended lifespan of the portable ultrasonic scanning apparatus 200.

Hereinafter, a connection operation between the portable ultrasonic scanning apparatus 200 and the battery based on a remaining charge of batteries will be described with reference to FIGS. 10 and 11.

The controller 250 monitors voltages of the first terminals 130 by sensing voltages of the relays 220, to judge whether or not the batteries 120 are mounted in the battery pack 100 (500). Then, the controller 250 judges whether or not a plurality of batteries 120 is mounted in the battery pack 100 (510). If one battery 120 is located in the battery pack 100, the controller 250 turns on the corresponding relay 220 (530). If a plurality of batteries 120 is located in the battery pack 100, the controller 250 turns on the relay 220 that connects one battery 120 and the power source unit 210 to each other, and turns off the other relays 220 (520).

The controller 250 judges whether or not a remaining charge of the battery 120 connected to the power source unit 210 is a reference value or less (540 and 550). If the remaining charge of the battery 120 is the reference value or less, the controller 250 turns on the relay 220 that connects another battery 120 and the power source unit 210 to each other, and turns off the relay 220 that connects the existing battery 120 and the power source unit 210 to each other (560). In this case, the display unit 280 displays the remaining charge of the battery 120 and as necessary, warns that the battery 120 is almost discharged. Also, the display unit 280 informs the user of replacement of the battery 120.

The above description exemplifies the relay 220 connecting the existing battery 120 and the power source unit 210 to each other as being turned off when the existing battery 120 is almost discharged. However, alternatively, if the charge of the existing battery 120 is reduced and the power source unit 210 is connected to the commercial power source via the power adaptor 310 as illustrated in FIG. 11, the relay 220 between another battery 120 and the power source unit 210 may be turned on, and the relay 220 connecting the existing battery 120 and the power source unit 210 to each other remains in a power-on state, to enable charging of the existing battery 120 (660).

In this case, the controller 250 judges whether or not the existing battery 120 is completely charged by checking the remaining charge of the existing battery 120. Upon completion of the charging, the controller 250 turns off the relay 220 that connects the existing battery 120 and the power source unit 210 to each other (670).

Figure 10:
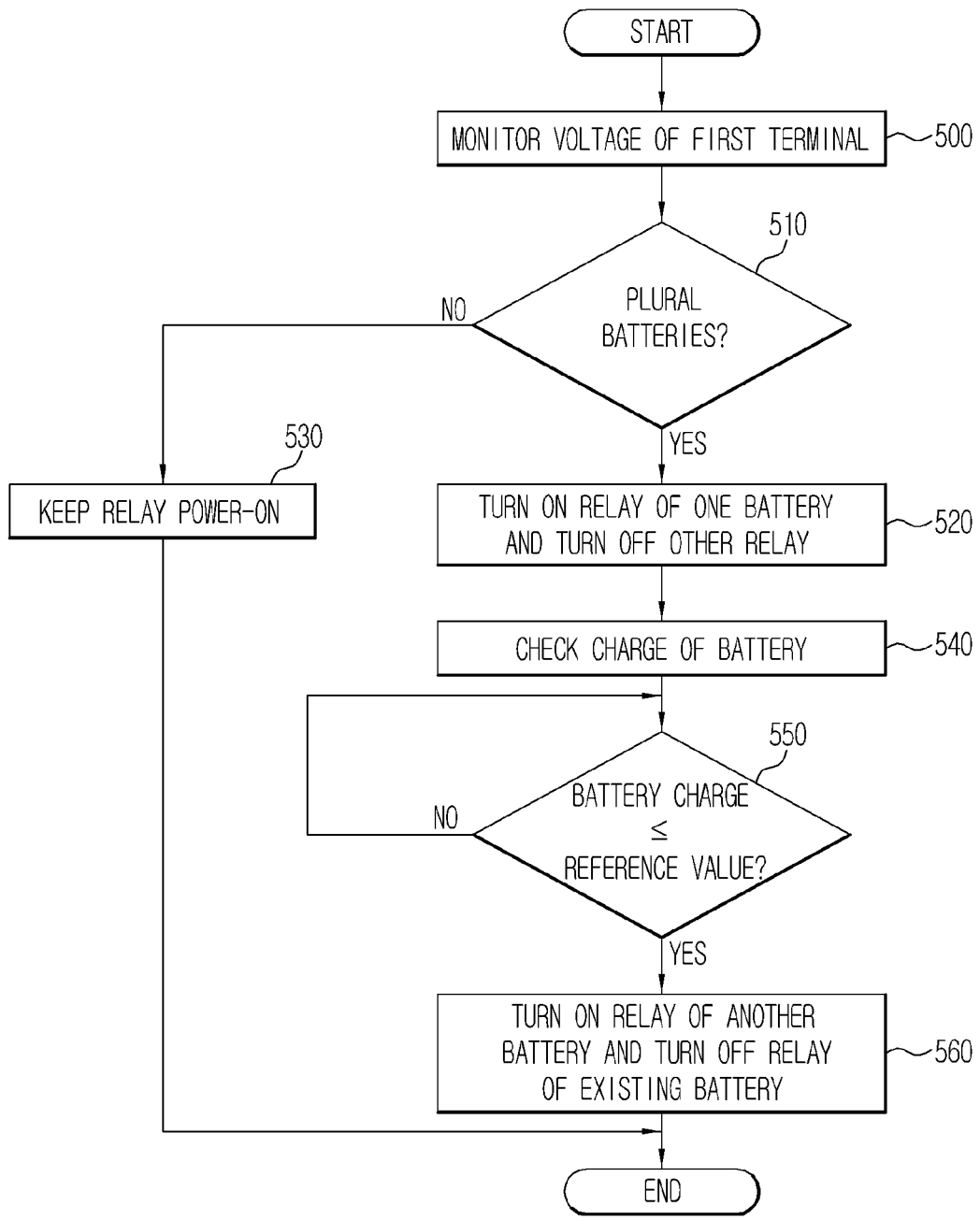
FIG. 10 is a control flowchart illustrating battery connection based on charge/discharge of a battery in a portable ultrasonic scanning apparatus according to an embodiment of the present disclosure.
Figure 11:
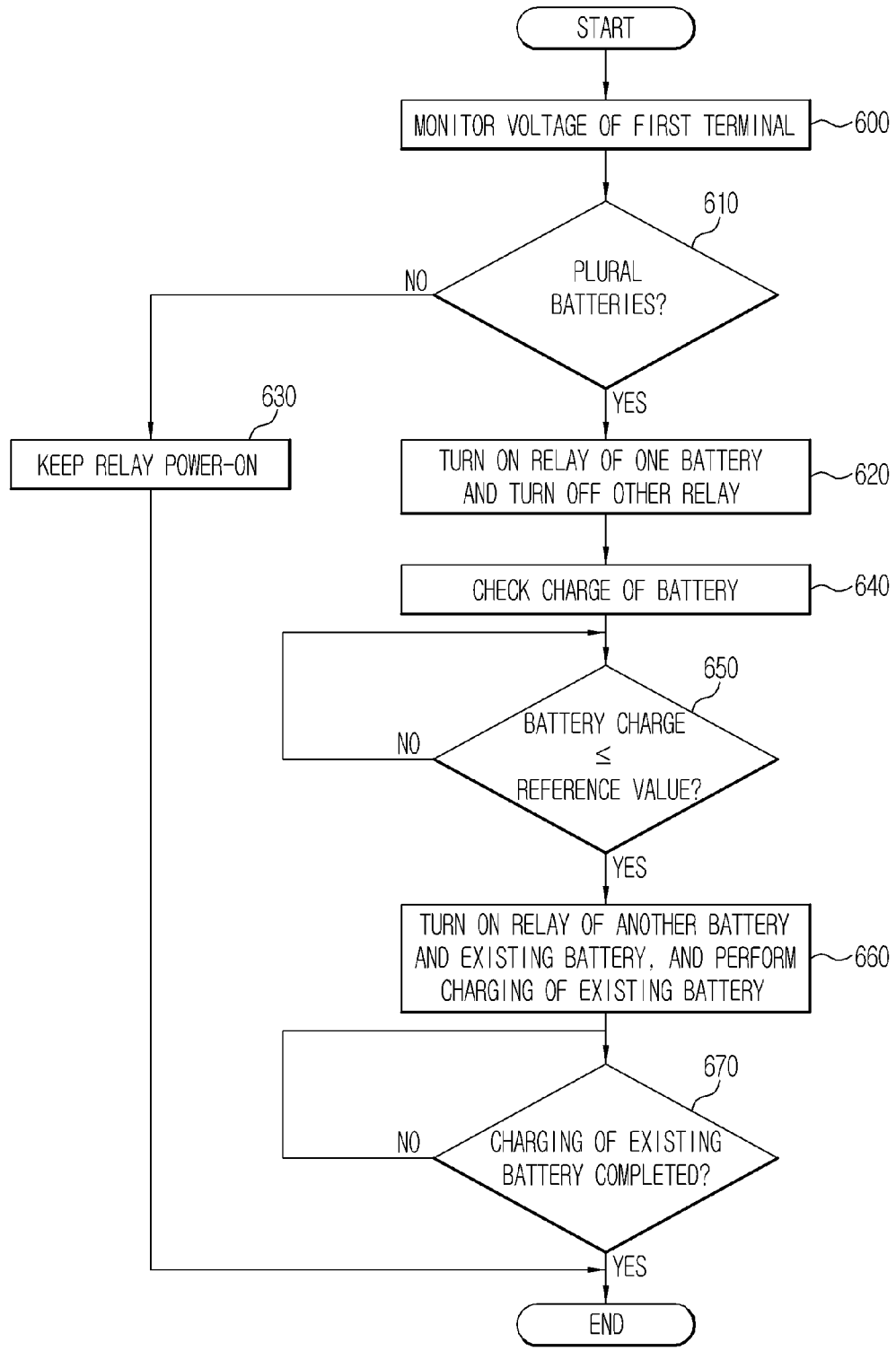
FIG. 11 is a control flowchart illustrating battery charge added to the battery connection of FIG. 10.

Other operations 600 to 650 of FIG. 11 are identical to those of FIG. 10 and a description thereof will be omitted.

Figure 12:
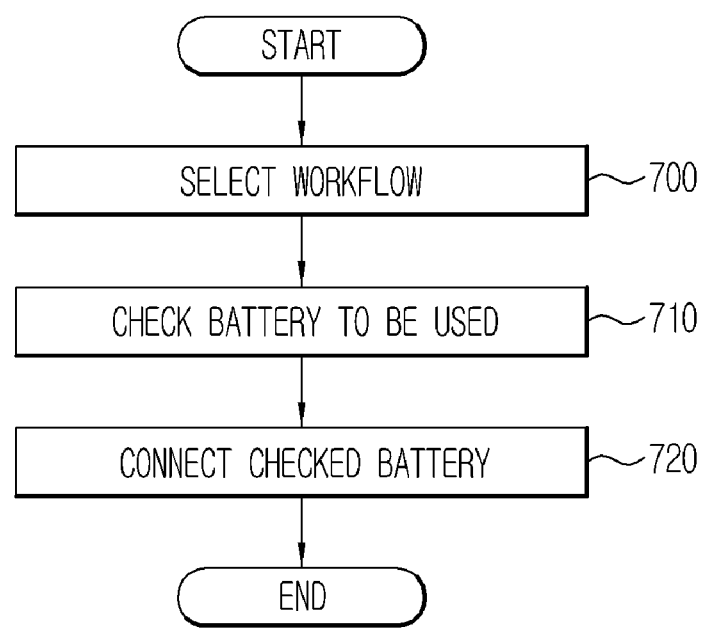
FIG. 12 is a control flowchart illustrating battery connection based on a workflow of a portable ultrasonic scanning apparatus according to an embodiment of the present disclosure.

Hereinafter, battery connection based on a workflow of the portable ultrasonic scanning apparatus according to an embodiment of the present disclosure will be described with reference to FIG. 12. If the user selects a workflow to be executed (700), the controller 250 checks a battery to be used upon execution of the workflow from the memory 241 (710). Then, the controller 250 turns on the relay 220 that connects the battery and the power source unit 210 to each other, and turns off the other relays 220 (720). As such, it may be possible to connect the battery suitable for each workflow to the portable ultrasonic scanning apparatus 200.

As is apparent from the above description, a sub-battery pack or battery pack according to an aspect of the present disclosure may be carried along with a portable ultrasonic scanning apparatus, ensuring convenient use thereof. Further, the sub-battery pack or battery pack may be directly connected to the portable ultrasonic scanning apparatus, or a battery mounted in the battery pack may be exchanged with a discharged internal battery of the portable ultrasonic scanning apparatus, which provides use convenience.

A portable ultrasonic scanning apparatus according to an aspect of the present disclosure may easily receive power from a sub-battery pack or battery pack that may be carried along with the portable ultrasonic scanning apparatus even if an internal battery thereof is discharged, which increases use convenience of the portable ultrasonic scanning apparatus. Further, since supply of power from the sub-battery pack or the battery pack may be possible, the portable ultrasonic scanning apparatus may be stably used for a long time without frequent charging thereof.

A cart according to an aspect of the present disclosure may realize not only stable connection between a battery pack and a portable ultrasonic scanning apparatus, but also convenient transportation thereof.

Although the embodiments of the present disclosure have been shown and described, it would be appreciated by those skilled in the art that changes may be made in these embodiments without departing from the principles and spirit of the inventive concept, the scope of which is defined in the claims and their equivalents.

What is claimed is:

1. A battery pack comprising:
   a case;
   at least one receptacle defined in the case and configured to accommodate at least one battery that supplies power to a portable ultrasonic scanning apparatus;
   at least one first terminal installed to the at least one receptacle, the at least one first terminal coming into contact with a terminal of the battery when the battery is accommodated in the at least one receptacle; and
   a second terminal electrically connected to the at least one first terminal, the second terminal being electrically connected to the portable ultrasonic scanning apparatus.

2. The battery pack according to claim 1, wherein the at least one receptacle includes plural receptacles partitioned from one another.

3. The battery pack according to claim 2, wherein the respective receptacles have different sizes of receiving spaces to accommodate different sizes of batteries.

4. The battery pack according to claim 3, wherein the respective receptacles have different widths or lengths.

5. The battery pack according to claim 1, wherein the first terminal is installed on a wall surface of the at least one receptacle.

6. The battery pack according to claim 1, wherein the second terminal is installed on an outer surface of the case.

7. The battery pack according to claim 1, wherein the at least one first terminal includes plural first terminals, and the plural first terminals are separate from one another with respect to the second terminal.

8. The battery pack according to claim 1, wherein the at least one first terminal includes plural first terminals, the plural first terminals are connected to one another in parallel, and the second terminal is connected in series to the plural first terminals.

9. A battery pack comprising:
   a first sub-battery pack including a first case, a first receptacle defined in the first case to accommodate a battery that supplies power to a portable ultrasonic scanning apparatus, and a first coupler installed to the exterior of the first case; and a second sub-battery pack including a second case, a second receptacle defined in the second case to accommodate a battery that supplies power to the portable ultrasonic scanning apparatus, and a second coupler installed to the exterior of the second case to enable coupling between the first sub-battery pack and the second sub-battery pack.

10. The battery pack according to claim 9, wherein each of the first and second sub-battery packs includes a first terminal installed on the first or second receptacle to come into contact with a terminal of the battery when the battery is mounted in the first or second receptacle, and a second terminal electrically connected to the first terminal, the second terminal being electrically connected to the portable ultrasonic scanning apparatus.

11. The battery pack according to claim 9, wherein the first coupler includes a boss, and the second coupler includes a groove for sliding coupling with the boss.

12. The battery pack according to claim 9, wherein the first and second couplers are disposed near corners of vertical outer surface edges of the first and second cases.

13. A sub-battery pack comprising:
a case;
a receptacle defined in the case and configured to accommodate a battery that supplies power to a portable ultrasonic scanning apparatus;
a first terminal installed to the receptacle, the first terminal coming into contact with a terminal of the battery when the battery is accommodated in the receptacle;
a second terminal electrically connected to the first terminal, the second terminal being electrically connected to the portable ultrasonic scanning apparatus; and
a coupler installed to the exterior of the case to allow the sub-battery pack to be coupled to another sub-battery pack.

14. The sub-battery pack according to claim 13, wherein the coupler includes a boss for sliding coupling with a groove formed in another sub-battery pack, or a recess for sliding coupling with a boss formed at another sub-battery pack.

15. The sub-battery pack according to claim 13, wherein the coupler is disposed near a corner of a vertical outer surface edge of the case.

* * * * *